United States Patent [19]

Wenman

[11] Patent Number: 5,408,864
[45] Date of Patent: Apr. 25, 1995

[54] METHOD OF DETERMINING THE AMOUNT OF GAS ADSORBED OR DESORBED FROM A SOLID

[75] Inventor: Richard A. Wenman, Coral Springs, Fla.

[73] Assignee: Coulter Corporation, Miami, Fla.

[21] Appl. No.: 80,433

[22] Filed: Jun. 18, 1993

[51] Int. Cl.$^6$ .......................................... G01N 15/08
[52] U.S. Cl. ..................................................... 73/38
[58] Field of Search ............................... 73/38, 865.5

[56] References Cited

U.S. PATENT DOCUMENTS

| | | | |
|---|---|---|---|
| 2,729,969 | 1/1956 | Innes | 73/38 |
| 2,788,657 | 4/1957 | Innes | 73/38 |
| 3,176,473 | 4/1963 | Andonian | 62/51.1 |
| 3,211,006 | 10/1965 | Haley, Jr. | 73/865.5 |
| 3,555,912 | 1/1971 | Lowell | 73/38 |
| 3,850,040 | 11/1974 | Orr, Jr. et al. | 73/37 |
| 4,489,593 | 12/1984 | Pieters et al. | 73/38 |
| 4,856,320 | 8/1989 | Bose et al. | 73/30.01 |
| 5,239,482 | 8/1993 | Ajot et al. | 73/38 |

OTHER PUBLICATIONS

British Standards Institution, BS 4359: Part 1: 1984, "Determination of the Specific Surface Area of Powders. Part 1. Recommendations for Gas Adsorption (BET) Methods."

Dollimore, D., Turner, A., "The BET Method of Analysis of Gas Adsorption Data and its Relevance to the Calculation of Surface Areas," *Surface Technology*, vol. 4, pp. 121–160.

Primary Examiner—Thomas P. Noland
Assistant Examiner—Michael J. Brock
Attorney, Agent, or Firm—Mitchell E. Alter

[57] ABSTRACT

A method of analyzing the characteristics of an adsorbent is provided. The method uses a sample chamber of known volume and known temperature with an adsorbent to be analyzed. An adsorptive gas which comprises at least 80 percent of a component gas and less than 20 percent of a carrier gas, at a temperature higher than its boiling point at environmental atmospheric pressure is introduced into the sample chamber. The pressure of the adsorptive gas is measured. The quantity of the adsorptive gas adsorbed by the adsorbent, at the measured pressure is determined. And, a relative pressure in the sample chamber and the quantity of the adsorptive gas adsorbed by the adsorbent at the relative pressure is correlated.

23 Claims, 2 Drawing Sheets

METHOD OF DETERMINING THE AMOUNT OF GAS ADSORBED OR DESORBED FROM A SOLID

TECHNICAL FIELD

The present invention relates to a super atmospheric, sub-critical temperature method for determining the amount of a gas adsorbed or desorbed by a solid in a manner such that the corresponding adsorption and/or desorption isotherms can be constructed, from which in turn various morphological characteristics of the solid such as surface area, pore size distribution, and pore volume, can be determined.

BACKGROUND OF THE INVENTION

The measurement of morphological characteristics of solids, such as catalysts, catalyst supports, pigments, clays, minerals, pharmaceutics, and composite materials is an important aspect of analytical chemistry and quality control for manufacturing of numerous products.

For example, a very useful morphological characteristic of a solid is its surface area. One of the most widely used techniques for surface area determination is that of gas sorption. Gas sorption techniques utilize a theoretical model wherein the surface of a solid, the adsorbent, is characterized as being covered by a monolayer of closely packed molecules of an adsorbed gas. After adsorption on to the adsorbent, the condensed, relatively non-mobile gas phase is referred to as the adsorbate; whereas, the highly mobile gaseous phase is referred to as the adsorptive. If one can determine the amount, usually expressed in millimoles, of adsorbate which forms the monolayer, the area which is covered by the monolayer can be calculated from the product of the number of molecules in the monolayer and the cross sectional area of each molecule. In 1938 Branauer, Emmett, and Teller (*J. Am. Chem. Soc.* Vol. 60, 2309) described a mathematical equation, referred to as the BET equation, for determining the amount of adsorbate in the monolayer from the adsorption isotherm of the adsorbate.

The adsorption isotherm is a plot of the amount of the adsorbate adsorbed on a solid adsorbent against either the relative pressure or the equilibrium pressure of the adsorbate at a constant temperature. In order to utilize the BET equation accurately to determine surface area, one must at least obtain a sufficient number of data points on the adsorption isotherm to be able to determine the point on the adsorption isotherm at which the "monolayer capacity" occurs. The "monolayer capacity" is a variable in the BET equation and represents the point on the adsorption isotherm, wherein a monolayer of closely packed adsorbed molecules is present at the surface of the adsorbent. Since the monolayer capacity generally occurred at prior to reaching an adsorptive relative pressure of 0.35, one desires to know the adsorption isotherm at least up to this value of relative pressure to be able to calculate the surface area from the BET equation. The adsorptive relative pressure is one way of expressing the equilibrium pressure of the adsorptive as a fraction of the pressure at which bulk condensation of the adsorptive occurs under any set of constant volume and temperature conditions. A concise review of the BET method appears in a publication by the British Standard Institution, BS 4359: Part 1: 1984, titled, "Determination of the Specific Surface Area of Powders-Part I Recommendations for Gas Adsorption (BET) Methods."

Adsorption isotherms can be determined by measuring the sample pressure and determining the amount of adsorbate adsorbed either with a volumetric or a gravimetric method. Use of this invention is applicable to both volumetric and gravimetric determinations of isotherms, although volumetric methods are preferred.

Three main volumetric techniques are in common use. These can be classified as static or fully equilibrated, continuous flow or quasi-equilibrated, and dynamic or chromatographic. Both the static and continuous flow techniques can be described as vacuum volumetric methods. However, in some publications, the dynamic technique has been described as continuous flow, although it does not use vacuum technology, but instead employs a non-adsorbing carrier gas and adsorptive mixture. For the purposes of this invention, the term "dynamic" is applied to all of the chromatographic types of sorption methods commonly used for rapid quality control analysis. As related to this invention, the static and continuous flow techniques are particularly applicable.

Volumetric methods conventionally employ a selected adsorptive at the most convenient temperature for adsorption. For example, when one uses the adsorptive nitrogen with an adsorbent sample to be tested, the adsorptive is cooled to a temperature of approximately 77K. The temperature of the adsorptive is provided by means of a liquid nitrogen bath in a dewar which is open to the atmosphere, and therefore the adsorptive has a boiling point equal to the environmental atmospheric pressure.

By definition, the boiling point of a liquid is the temperature of the liquid at which its vapor pressure is equal to atmospheric pressure. When using liquid nitrogen, the boiling point is at a temperature at which the vapor pressure of the liquid nitrogen is equal to or slightly greater than the atmospheric pressure of the environment.

Consequently, since both the adsorbent and the adsorptive are cooled with the liquid nitrogen bath which is open to the atmosphere, the adsorptive gas and the adsorbent sample have a temperature equal to the boiling point of the liquid nitrogen bath. Because of variations in atmospheric pressure which affect the open dewar, or impurities in the liquid nitrogen bath which affect the saturation vapor pressure of the liquid nitrogen, the normal boiling point temperature of the liquid nitrogen changes very slightly from those reported at exactly one atmosphere pressure.

The reason that the adsorptive is cooled to the boiling point of liquid nitrogen is because it is recognized by those skilled in the art that the quantity of physically adsorbed gas at a given relative pressure (a fraction of saturation pressure) increases with decreasing temperature. Consequently, consistent with practical limits, the lowest most conveniently achieved temperature is chosen to provide maximum measurement sensitivity.

Volumetric devices typically consist of a gas storage unit and a vacuum source unit connected in parallel to a volumetric measuring device of known Volume $V_1$, referred to as the doser unit or the manifold unit. The doser unit can be connected alternately to either the vacuum unit or the gas storage unit by a series of valves. The doser unit in turn is connected in series through another valve to a sample unit, a chamber of known Volume $V_2$, which holds the solid sample to be tested.

By manipulating the appropriate valves, the doser and sample units are evacuated and the evacuated doser is sealed off from the evacuated sample chamber. Nitrogen is permitted to slowly enter and fill the doser unit from the gas storage unit to a targeted pressure, at which time the valves are closed to seal off the doser, and the nitrogen pressure therein is measured. When a constant pressure $P_1$ in the doser is achieved, the valve separating the sample chamber and doser is opened allowing the adsorptive, typically $N_2$, in the doser to expand into the sample chamber.

The sample chamber and doser together define a third Volume $V_3$ (i.e. $V_1+V_2$). When the pressure in $V_3$ is constant, indicative of adsorption equilibrium, it is measured. This equilibrium pressure is used to calculate the total number of moles of $N_2$ that remains in the gas phase. The number of moles of $N_2$ adsorbed on the solid is equal to the number of moles of $N_2$ initially present in Volume $V_1$ of the doser, plus the number of moles of $N_2$ in the sample chamber defining Volume $V_2$ (the number of moles in Volume $V_1$ for the initial run is 0, but increases with each successive run), less the number of moles of gaseous $N_2$ in Volume $V_3$, after equilibrium. The combined data of the amount of $N_2$ adsorbed at a particular equilibrium pressure constitutes a single point on the adsorption isotherm. The above procedure is repeated to obtain additional points on the adsorption isotherm. Each successive dose increases the pressure in the sample chamber until, at approximately atmospheric pressure, the sample becomes completely saturated with condensed $N_2$. At this saturation point, bulk condensation of $N_2$ takes place around the sample and in the free space in the sample holder. Conventional practice is to generate about 3 to 10 data points on the adsorption isotherm for surface area determinations. A detailed summary of this method is provided in the review paper, "The BET Method of Analysis of Gas Adsorption Data and Its Relevance to the Calculation of Surface Areas" by Dollimore, D., Sponner, P., and Turner, A., *Surface Technology*, Vol. 4, p. 121-160 (1976).

However, with manual dosing methods, exact target pressures are rarely achieved and several additional unwanted data points can be obtained. While the adsorptive gas is being dosed to the manifold in order to reach an estimated required pressure, an increase above the pressure desired can be obtained. If this higher than required pressure is dosed to the sample, significant loss of operational range can result if too much gas is adsorbed. It is normal practice to open the nitrogen gas adsorptive valve very carefully. This valve typically is capable of supplying nitrogen to higher than atmospheric pressure. If an increase above the pressure desired does occur, then it must be removed by judicious opening of the vacuum valve, before adsorption. Additional pressure stabilizing time is always required and typically is equal to one or two minutes. This time is in addition to the sorption equilibrium time.

A capillary method having a continuous flow of the adsorptive is disclosed in U.S. Pat. No. 2,729,969 to Innes. Innes teaches a method for the measurement of surface areas greater than 0.5 meter per gram, which comprises introducing nitrogen gas at a constant flow rate into an evacuated system containing a weighed sample amount which is cooled to $-195°$ C., measuring the time required for the vacuum in the evacuated system to decrease from 29.6" to 23.7" of mercury and calculating from the time required the surface area of the material. Innes further teaches that due to impurities present in the liquid nitrogen cooling bath, the bath temperature is somewhat higher than the boiling point of pure nitrogen. As a result, the saturation vapor pressure is slightly above one atmosphere. It has been reported elsewhere that dissolved impurities usually increase the bath temperature sufficiently to cause the vapor pressure of pure liquid nitrogen in the sample cell to increase by 10 to 20 mm Hg above ambient pressure. Innes further discloses that other gases such as n-butane, argon, $CO_2$, CO, and gases having a vapor pressure of about one atmosphere at 50 to 225K can be employed for area and pore volume measurements. However, the Innes method suffers from environmental induced flow rate fluctuations and imprecise equilibrium pressure conditions, which affect the accuracy of measurement.

The just-mentioned and other similar problems have been addressed in U.S. Pat. No. 4,489,593 to Pieters, et al.

Innes and Pieters, et al. disclose using an adsorptive at a temperature at which the adsorptive condenses at approximately one atmosphere pressure and introducing the adsorptive into the sample holder containing the substance to be analyzed at a constant flow rate. Pieters et al. teach controlling the flow rate by the use of a mass flow controller. By using such techniques, the flow rate approximates the adsorptive equilibration rate of adsorption. By controlling the mass flow rate to be not greater than the equilibration rate of adsorption, the pressure established, at any given time during the introduction of the adsorptive, will be the equilibrium pressure. This is significant because the adsorption isotherm is a plot of the amount of adsorptive adsorbed at a given equilibrium pressure. Consequently the determination of the adsorption isotherm is simplified. However, owing to the flow rate being not greater than the equilibration rate of adsorption, flow times of about four hours are required. Moreover, it is generally recognized that the equilibration rate of adsorption can vary according to the physical and chemical characteristics of the sample.

Another technique for determining adsorption isotherms has been reported in Nelsen & Eggersten, Analytical Chem., Vol. 30, p. 13-87 (1958), "Adsorption Measurements By A Continuous Flow Method." In this dynamic technique, nitrogen is adsorbed by the adsorbent at a liquid nitrogen temperature from a gas stream of nitrogen and helium, and eluted upon warming the sample. The nitrogen liberated is measured by a thermal conductivity detector. Thus, the amount of adsorbed gas is determined by concentration measurements in a continuous flow system at atmospheric pressure, rather than by pressure volume measurements at below atmospheric pressure. This method is referred to herein as a chromatographic method for determining adsorption isotherms because of its resemblance to chromatography techniques. Two requirements of this method are steady flow of carrier and adsorbate gases, and thorough mixing of the two gases, in situ.

A typical continuous flow process (dynamic technique) is defined in U.S. Pat. No. 3,211,006 to A. J. Haley, Jr. In Haley, Jr., a thermal conductivity cell is employed as a detector for the amount of adsorption from an operating gas mixture, which is a maximum of approximately fifty percent (50%) nitrogen at operating pressure of slightly over atmospheric to about 200 atmospheres. However, this continuous method requires several different inert carrier gas/adsorbate gas mixtures to determine the isotherm. As such, the gas mixtures typically are expensive to purchase pre-mixed. Alternatively, it is time-consuming to obtain the gas mixture by mixing gases which would require two mass flow controllers, each of which will contribute to inaccuracy of measurement.

In a similar dynamic method (continuous flow), U.S. Pat. No. 4,856,320 to Bose et al. employs operating pressures from approximately 0.5 to 116 atmospheres, an operating temperature of approximately 25° C. and measuring the dielectric constant of the gas to determine the amount of gas adsorbed. Bose et al. teach that the volumetric method is reliable at low pressure when all gases in the bulk phase closely resemble the ideal gas. However, the Bose et al. method lacks precision resulting from small adsorption volumes and use of polar gases or very high pressures which affects the second dielectric virial coefficient.

Desorption isotherms are important because various mathematical equations have been developed to enable one skilled in the art to determine certain morphological characteristics of solids. More specifically, adsorption, as well as desorption isotherms enable one to calculate the pore size distribution of a solid sample from the data embodied therein. A desorption isotherm is a plot of the amount of a preadsorbed gaseous material, the desorbate, desorbed from a solid against the equilibrium pressure or relative pressure of the desorbate at a constant temperature. After desorption from a solid sample, the desorbent, the gas is referred to as the desorptive. The desorption isotherm differs from the adsorption isotherm in that it is constructed starting with a solid, saturated with the desorbate, and gradually reducing the pressure over the solid to near absolute vacuum. In contrast, the adsorption isotherm starts with an evacuated solid sample and increases the pressure of a gaseous adsorptive in contact therewith until sample saturation is reached. The adsorption and desorption isotherms are collectively known as the sorption isotherm.

Gas-solid interaction can cause at least a portion of the desorption path of the sorption isotherm to lie higher on the isotherm plot than the adsorption path. The failure of the desorption path to duplicate the adsorption path of the isotherm is referred to as hysteresis. The two most common forms of hysteresis are closed loop and open loop. In the closed loop hysteresis behavior, the desorption path of the isotherm eventually rejoins the adsorption path at some low relative pressure. Closed loop hysteresis normally is associated with porosity in the sample being tested.

For example, at the start of the desorption isotherm, the pores of the sample are saturated and filled with the desorbate. As desorption occurs, capillary action delays desorption of the desorbate present within the pores, such that a lower pressure is required to evacuate the pores relative to the pressure which initiated the filling of the pores during adsorption. This delay is expressed as closed loop hysteresis behavior of the sorption isotherm. Open loop hysteresis is characterized by the failure of the desorption path of the isotherm to rejoin with the adsorption path. Open loop hysteresis usually is associated with some measurable amount of irreversible adsorption, which typically occurs when the gas reacts with the solid sample upon adsorption, conventionally referred to as chemisorption. Consequently on desorption, less material will desorb than was initially adsorbed, giving rise to an open loop in the sorption isotherm.

By intentionally inducing chemisorption, much can be learned about the surface of the solid sample. For example, chemisorption can be employed to determine the percent dispersion and surface area of microscopic particles of a catalyst deposited on a support by employing a gaseous adsorbate which will undergo chemisorption with the catalyst particles but not the support.

Other information in the substantially complete sorption isotherm permits the determination of total pore volume, average pore size, and pore shape, for example, slits versus cylindrical pores.

The above discussion highlights only a few of the incentives for obtaining substantially complete pictures of the entire sorption isotherm rather than narrow segments thereof, and any method or device capable of producing substantially complete sorption isotherms quickly and accurately possesses substantial advantages.

In view of the above, it is evident that there has been a continuing search for a quicker, simpler, and more accurate methods for determining surface area and sorption isotherms. The present invention was developed in response to this search.

SUMMARY OF THE INVENTION

One aspect of the present invention provides a method for determining the amount of an adsorptive gas adsorbed by a solid adsorbent so that a sorption isotherm can be constructed. In this adsorption mode, this method employs an adsorptive gas of known pressure and known volume at a temperature higher than its boiling point at the environmental atmospheric pressure. Preferably, the adsorptive has a saturation vapor pressure higher than its saturation vapor pressure at the environmental atmospheric pressure.

In a first embodiment of the adsorption mode, the method of analyzing the characteristics of an adsorbent comprises providing a sample chamber of known volume, known pressure and known temperature with an adsorbent to be analyzed; introducing into said sample chamber an adsorptive gas which comprises at least 80 percent of a component gas and less than 20 percent of a carrier gas, at a temperature higher than its boiling point at the environmental atmospheric pressure; measuring the pressure of said adsorptive gas at a relative pressure from 0 to 1; determining the quantity of said adsorptive gas adsorbed by said adsorbent, at said measured pressure; and correlating the relative pressure in said sample chamber and said quantity of the adsorptive gas adsorbed by said adsorbent at said relative pressure.

In a second embodiment of the adsorptive mode, the flow rate of the adsorptive gas is controlled, such that it is approximately equal to the equilibrium rate of adsorption, so that the sampled chamber pressure is approximately equal to the adsorptive gas equilibrium pressure. In this embodiment, the method of analyzing the characteristics of an adsorbent comprises providing a sample chamber of known volume, known pressure and known temperature with an adsorbent to be analyzed; introducing into said sample chamber an adsorptive gas which comprises at least 80 percent of a component gas and less than 20 percent of a carrier gas, at a temperature higher than its boiling point at the environmental atmospheric pressure, and at a known mass flow rate for a time sufficient to obtain adsorption of at least a portion of said adsorptive gas by said adsorbent, said known mass flow rate being not greater than the equilibration rate of adsorption of said adsorptive gas by said adsorbent; establishing the equilibrium pressure of said adsorptive gas as it is introduced into said sample chamber as a function of time, said equilibrium pressure being the sampled chamber pressure; and correlating the adsorptive gas sampled chamber pressure, the adsorptive gas mass flow rate, and the time needed to attain said sampled chamber pressure with the amount of adsorptive gas adsorbed by the adsorbent at said sampled chamber pressure.

Another aspect of the present invention provides a method for determining the amount of a desorptive gas desorbed by a desorbent, so that a sorption isotherm can be constructed. In this desorption mode, this method employs a desorptive gas of known pressure and known volume at a temperature higher than its boiling point at the environmental atmospheric pressure. Preferably, the desorptive gas has a saturation vapor pressure greater than its saturation vapor pressure at the environmental atmospheric pressure.

In a first embodiment of the desorption mode, the method of analyzing the characteristics of a solid desorbent saturated with a desorbate comprises providing a sample chamber of known volume, known pressure and known temperature with a desorbent for analysis, said desorbent having a desorptive gas condensed thereon; withdrawing from said sample chamber said desorptive gas, said desorptive gas comprising at least 80 percent of a single component gas and less than 20 percent of a carrier gas, at a temperature higher than its boiling point at the environmental atmospheric pressure; measuring the pressure of said desorptive gas at a relative pressure from 1 to 0; determining the quantity of said desorptive gas desorbed by said desorbent, at said measured pressure; and correlating the relative pressure in said sample chamber and said quantity of the desorptive gas desorbed by said desorbent at said relative pressure.

In a second embodiment of the desorption mode, the flow rate of the desorptive gas is controlled, such that it is approximately equal to the equilibrium rate of desorption, so that the sampled chamber pressure is approximately equal to the desorptive gas equilibrium pressure.

In this embodiment, this method of analyzing the characteristics of a solid desorbent saturated with a desorbate comprises providing a sample chamber of known volume, known pressure and known temperature with a desorbent for analysis, said desorbent having a desorptive gas condensed thereon and in equilibrium with a chamber atmosphere consisting of said desorptive gas; withdrawing from said sample chamber said desorptive gas, said desorptive gas comprising at least 80 percent of a component gas and less than 20 percent of a carrier gas, at a temperature higher than its boiling point at the environmental atmospheric pressure, at a known mass flow rate which is not greater than the equilibration rate of desorption of the desorptive gas from the desorbent for a time sufficient to obtain desorption of at least a portion of said desorptive gas by the desorbent; establishing the equilibrium pressure of said desorptive gas as it is withdrawn from said sample chamber as a function of time, said equilibrium pressure being the desorptive gas sampled chamber pressure; and correlating the desorptive gas sampled chamber pressure, the desorptive gas mass flow rate, and the time needed to attain said sampled chamber pressure with the amount of desorptive gas desorbed by the desorbent at said sampled chamber pressure.

BRIEF DESCRIPTION OF THE DRAWINGS

FIG. 1 omits certain features which those skilled in the art would recognize as desirable in actual apparatus operation. These omissions are made in order to simplify the presentation of the invention and to avoid encumbering it with well understood engineering details. Thus, for example, certain equipment obviously needed for a power supply, for electrical connections of solenoid valves, for computer automation, and other such details are omitted from the representation.

DETAILED DESCRIPTION OF THE INVENTION

Figure 1:
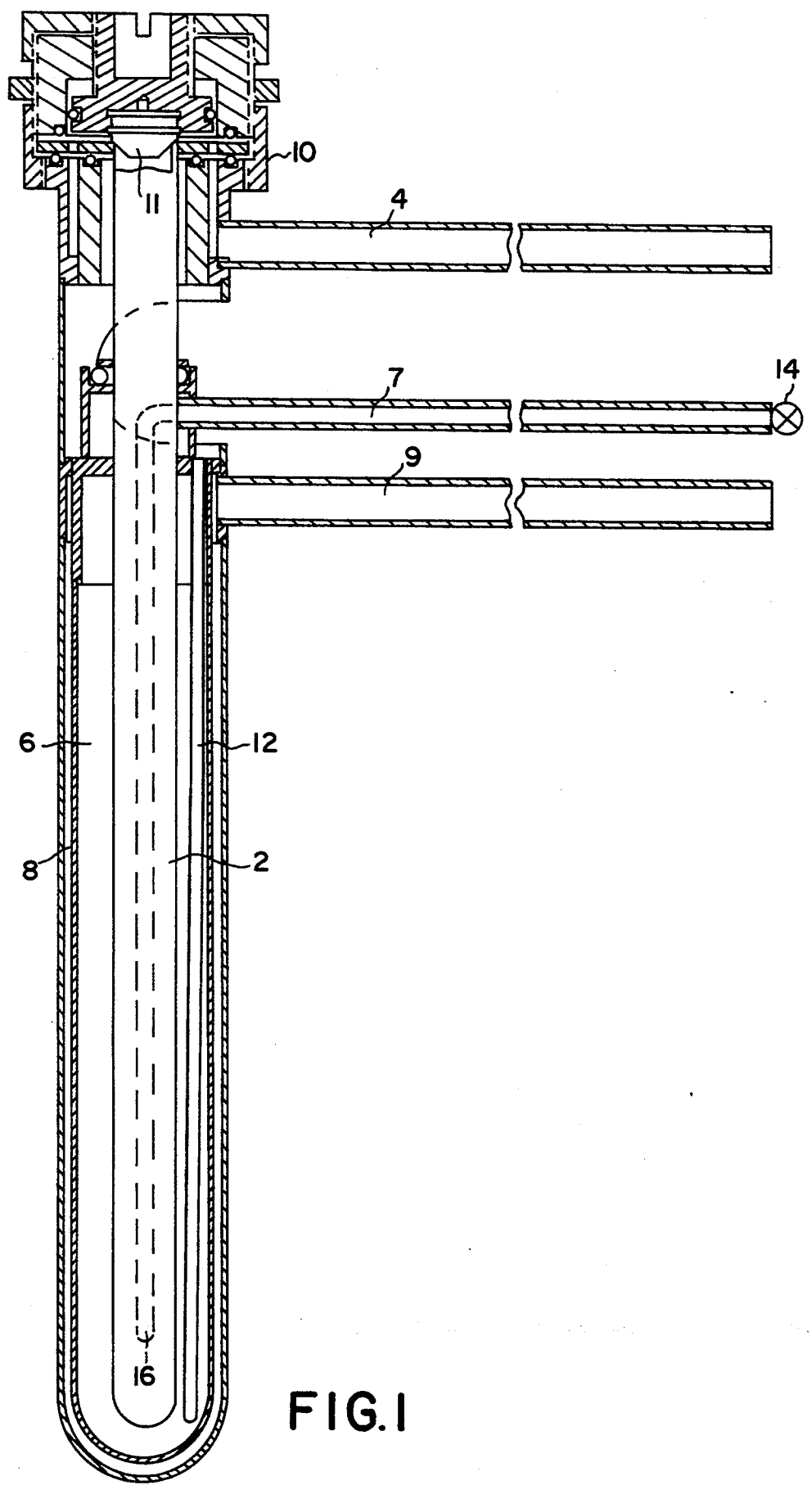
FIG. 1 is a side elevation, partly in section, of a preferred apparatus used with both the static and continuous flow methods to develop a sorption isotherm.

The present invention involves static and continuous flow techniques, which are vacuum volumetric methods. The process of the present invention can be conducted in an adsorption mode, in a desorption mode, or a combination of the two, wherein the adsorption mode is followed by the desorption mode.

The adsorption mode is conducted using a substance existing initially as a gas vapor, referred to herein as the adsorptive, and a solid sample, referred to herein as the adsorbent or sample. During the course of the adsorption mode, the adsorptive is adsorbed by the adsorbent. Thereafter, the adsorptive that is adsorbed is referred to as the adsorbate. The identity of the adsorptive will vary depending on whether the nature of the adsorption is intended and controlled to be physical, or physical and chemical. It is known that the adsorption phenomena can be the result of a physical or a physical and chemical process depending on the system involved and the temperature employed. Physical adsorption, frequently referred to as van de Waals' adsorption, is the result of a relatively weak interaction between solid and gas. One of the characteristics of this type of adsorption is that all the gas adsorbed by the solid can be removed therefrom by evacuation at about the same temperature at which it was adsorbed. For physical adsorption, the adsorptive is selected to be chemically inert with respect to the adsorbent.

Representative examples of adsorptives conventionally employed for physical adsorption include nitrogen, argon, krypton, oxygen, xenon, neon, helium, carbon dioxide and hydrocarbons, such as methane, butane, hexane and benzene. The adsorptive gas can comprise a component gas and an inert carrier gas. Preferably the adsorptive gas comprises at least 80 percent of a single component gas and less than 20 percent of a carrier gas. Most preferably, the adsorptive gas comprises a single gas without a carrier gas.

Since the quantity of physically adsorbed gas or vapor at a given pressure increases with decreasing temperature, the adsorptive typically is selected so that it will liquify at very low temperatures, These low temperatures correspond to the boiling points at atmospheric pressure of conventionally employed adsorbates which are noted in the following table.

TABLE 1

|  | Standard Boiling Point at 1 atmosphere (K) |
|---|---|
| Liquid Nitrogen | 77.35 |
| Liquid Argon | 87.45 |
| Krypton | 120.45 |
| Oxygen | 90.18 |
| Xenon | 166.05 |
| Neon | 27.10 |
| Helium | 4.2 |
| Air (21% $O_2$) | 78.8 |
| Methane | 111.66 |
| Butane | 272.5 |
| Hexane | 341.7 |
| Benzene | 353.1 |
| Carbon dioxide | 194.5 |

The identity of the adsorbent or sample can be any solid sought to be analyzed for its morphological characteristics, such as surface area. The methods described herein are applicable to a sample having a surface area of typically from about 0.001 to about 2000 m²/g, preferably from about 0.05 to about 1500 m²/g, and most preferably from about 0.5 to about 1000 m²/g; and pore size radii of typically from about 0.35 to about 300 nanometers, preferably from about 0.5 to about 100 nanometers, and most preferably from about 0.5 to about 50 nanometers.

Before determining the amount of adsorptive adsorbed by a sample, the sample is placed in the sample chamber and cleansed of impurities by removing adsorbed atmospheric gases, such as nitrogen, oxygen, and water vapor. This process is referred to as outgassing. The process is achieved by conventional methods known to those skilled in the art. Examples of such methods are described in Orr, C. and Dallavalle, J., "Fine Particle Measurement" Macmillan Co., p. 164-204 (1960). One such disclosed example includes heating the sample in a vacuum at temperatures of about 110° to about 600° C. for a period of from about 4 to about 12 hours. The sample weight and density can also be determined in accordance with conventional methods before the sample is contacted with the adsorptive.

Thereafter and in accordance with procedures known to those skilled in the art, the overall volume of the sample chamber is determined. In addition, the volume of the sample in the chamber is determined by procedures known to those skilled in the art and designated as the "dead space"; whereas, the remaining volume of the sample chamber and the piping between it and the manifold doser is designated as the "free space." Typically, helium gas is chosen to be used to determine the dead space, because it is substantially inert and also because there is no appreciable adsorption of helium by the sample materials at the cryogenic temperature of the sample.

Using methods known to those skilled in the art, the free space is determined by the conventional method of precharging the doser unit to a predetermined pressure, and then permitting the helium in the doser unit to expand into the sample chamber. The reduction in pressure in the doser unit can be converted by those skilled in the art by use of standard computation techniques to a value which represents a corresponding number of cubic centimeters of helium gas, taken at the reference temperature and pressure.

A preferred method to determine the free space is to use helium at above atmospheric pressure. By using helium at above atmospheric pressure, the sample outgassing period is reduced. This results in a decrease in the total analysis time for determining the isotherm. More specifically, when determining the free space, helium is employed at a pressure ranging from 0.1 to 100 atmospheres, preferably from 1 to 80 atmospheres and more preferably from 1 to 30 atmospheres.

By employing helium at the elevated pressure to determine the free space, the typical contaminates such as water, air, oxygen, and carbon dioxide are partially removed together with the helium during the subsequent evacuation stage. The typical contaminants are removed by the helium due to its carrier gas capability. By performing successive free space measurements, which typically require only one to two minutes to perform, the contaminates are more effectively washed from the sample. Although this method of removing impurities does not provide the greatest degree of accuracy when subsequent isotherms are measured, the expected accuracy of surface area measurement is within five to ten percent of that obtained when thorough outgassing is employed. However, in the present method, the use of higher than atmospheric pressures for the measurement of sorption isotherms, reduces the inaccuracies produced if a sample is not fully outgassed. More specifically, a small outgassing rate or an increase in the sample pressure during the sorption measurement due to the contribution of the vapor pressure of contaminants, such as water, is minimized when the method employs 10 atmospheres pressure instead of the conventional 1 atmosphere pressure.

After the free space of the sample chamber has been determined, sample analysis is commenced. According to the present method, the adsorptive gas in the sample chamber will be at a temperature greater than the environmental atmospheric boiling point of the adsorptive gas.

In order to obtain the adsorptive at a temperature greater than the boiling point of the adsorptive gas at environmental atmospheric pressure, the adsorptive must be in a pressurized container and heated to a temperature higher than its corresponding environmental atmospheric boiling point. For example, when using a liquid nitrogen cooling bath to cool a nitrogen adsorptive, the nitrogen bath must be pressurized and heated to a temperature higher than its corresponding environmental atmospheric boiling point. If the nitrogen cooling bath in which the sample chamber is immersed has a pressure greater than atmospheric, such as 800 mm Hg, then the nitrogen adsorptive boiling point will correspond to the temperature at which the adsorptive will have a vapor pressure equal to 800 mm Hg.

The adsorptive is maintained at about 5K to 373K (−268° C. to 100° C.) and preferably from 65K to 150K (−208° C. to −123° C.) and more preferably from 78K to 125K (−195° C. to −148° C.) and most preferably from 80K to 110K (−193° C. to −163° C.) Preferably the adsorptive has a temperature higher than 0.2K above the boiling point of the adsorptive at environmental atmospheric pressure, and more preferably 0.5K and most preferably 1K above the boiling point of the adsorptive at environmental atmospheric pressure.

Table 2 correlates the relationship between nitrogen temperature and its corresponding vapor pressure.

TABLE 2
Temperature versus nitrogen vapor pressure

| Temperature (K) | Vapor Pressure Atmospheres | mm Hg |
| --- | --- | --- |
| 76 | 0.8506 | 646.5 |
| 77.347 | 1.0000 | 760.0 |
| 78 | 1.0793 | 820.3 |
| 82 | 1.6739 | 1,272.2 |
| 86 | 2.4865 | 1,889.7 |
| 88 | 2.9882 | 2,271.0 |
| 90 | 3.5607 | 2,706.1 |
| 100 | 7.6885 | 5,843.3 |
| 104 | 10.041 | 7,631.2 |
| Critical Temperature 126.2K | Critical Pressure 33.55 Atmospheres | |

In traditional static and continuous flow techniques, the adsorptive nitrogen gas and adsorbent are maintained at approximately the boiling point temperature of the adsorptive and at a saturation vapor pressure of one atmosphere. The adsorptive gas is considered to be at approximately its environmental atmospheric boiling point because the sample chamber is cooled by a cryogenic liquid nitrogen bath open to the environment. As appreciated by those skilled in the art, the temperature of the adsorptive in the conventional isotherm measurement can change slightly due to environmental conditions in the liquid nitrogen bath. Table 3 demonstrates the gradual increase in temperature of the liquid nitrogen bath that typically occurs due to oxygen, carbon dioxide and water vapor contaminants which are from the environment.

TABLE 3
Time-Temperature of a Liquid Nitrogen Bath

| | | | |
| --- | --- | --- | --- |
| 0 min. | 77.103K | 90 min. | 77.128K |
| 5 | 77.106 | 95 | 77.143 |
| 10 | 77.099 | 100 | 77.155 |
| 15 | 77.079 | 105 | 77.130 |
| 20 | 77.090 | 110 | 77.121 |
| 25 | 77.086 | 115 | 77.130 |
| 30 | 77.095 | 120 | 77.129 |
| 35 | 77.104 | 125 | 77.137 |
| 40 | 77.077 | 130 | 77.128 |
| 45 | 77.083 | 135 | 77.144 |
| 50 | 77.101 | 140 | 77.154 |
| 55 | 77.071 | 145 | 77.162 |
| 60 | 77.104 | 150 | 77.171 |
| 65 | 77.107 | 155 | 77.183 |
| 70 | 77.112 | 160 | 77.200 |
| 75 | 77.114 | 165 | 77.208 |
| 80 | 77.122 | 170 | 77.225 |
| 85 | 77.124 | 175 | 77.218 |
| | | 180 | 77.227 |

The fluctuations in the temperature are attributed to the thermal currents within the liquid nitrogen bath. As noted, the increase in temperature of the liquid nitrogen bath increases approximately 0.12K over a three hour period.

The temperatures noted above were obtained in an open dewar containing liquid nitrogen. The liquid nitrogen was not replenished during the measurement. The boiling point of the liquid nitrogen was determined to be at 769.3 mm Hg pressure. In addition, the boiling point of fresh nitrogen was observed to be approximately 77.10K. The difference between the observed boiling point temperature and the standard textbook value reported, might be attributed to the accuracy of the temperature probe and environmental atmospheric conditions.

As appreciated by one skilled in the art, the saturation vapor pressure is determined by prior art methods so that sorption measurements can be made at relative pressures from 0 to 1. To determine the saturation vapor pressure, the prior art supplies a predetermined high pressure of the adsorptive into a vapor pressure thermometer. Thereafter, the vapor pressure thermometer is placed into a cooling medium, which causes a small amount of the gaseous adsorptive to condense; thereby establishing the saturation vapor pressure of the adsorptive at a temperature which is also the temperature at which subsequent analysis of the sample chamber occurs.

As taught by U.S. Pat. No. 3,850,040 to Orr, Jr. et al., when using nitrogen as the adsorptive, the saturation vapor pressure is determined by precharging the vapor pressure thermometer with nitrogen to a predetermined high pressure, such as 850 mm Hg, and thereafter placing the vapor pressure thermometer into an open dewar filled with liquid nitrogen. The lowering of the temperature of the vapor pressure thermometer causes a small amount of the gaseous nitrogen in the vapor pressure thermometer to condense; thereby establishing the saturation vapor pressure of nitrogen at a temperature which also is used for subsequent analysis of the sample chamber. It will be understood that this saturation vapor pressure for nitrogen can be used to calculate the saturation vapor pressure for another gas in the event that such other gas is used in place of nitrogen for the gas sorption analysis.

By using similar principles, the saturation temperature can be determined. To determine the saturation temperature, a vapor pressure thermometer is precharged with the adsorptive to a predetermined high pressure. Thereafter, the vapor pressure thermometer is cooled by the cooling medium. When the adsorptive is at equilibrium between the vapor and liquid phases, the temperature is measured, which is also the saturation temperature used in subsequent analysis of the sample chamber.

In the present method to develop the isotherm, preferably the adsorptive has a saturation vapor pressure higher than its saturation vapor pressure at the environmental atmospheric pressure. In order to obtain the adsorptive at a saturation vapor pressure greater than its saturation vapor pressure at the environmental atmospheric pressure, the adsorptive must be heated to a temperature higher than its corresponding boiling point at the environmental atmospheric pressure. Preferably, the adsorptive gas has a saturation vapor pressure greater than 0.05 atmospheres above its saturation vapor pressure at environmental atmospheric pressure. More preferably, the saturation vapor pressure is 0.1 atmospheres, and most preferably, 0.5 atmospheres above its saturation vapor pressure at the environmental atmospheric pressure.

The sorption measurements are made at absolute pressures from 0 up to the critical pressure of the adsorptive gas. Preferably, the absolute pressures are from 0 to 50 atmospheres, more preferably from 0 to 40 atmospheres, and most preferably from 0 to 34 atmospheres. For the adsorptive nitrogen, the pressure will preferably range from 0 to 33.55 atmospheres, the higher pressure corresponding to nitrogen's critical pressure. For nitrogen, the more preferred range for the absolute pressure during which sorption measurements are made are from 0 to 20 atmospheres, and most preferred from 0 to 15 atmospheres.

The increase in sample chamber pressure will have several advantages. First, above atmospheric gas pressures are very easy to control with conventional pneumatic equipment. For example, a relatively large volume of gas can be maintained at a constant pressure via a relieving pressure regulator. If this constant pressure source has a volume, which is large relative to the volume of the gas to be adsorbed on the sample, it can be used to supply repetitive small doses with minimal setup time, while reducing the possibility of pressure overshoot. Second, it is important that impurities such as oxygen, carbon dioxide or water vapor are not present within the adsorptive. Above atmospheric pressures ensure that if there are any leaks in the sample chamber, they occur out of the sample chamber and not into the sample chamber. This reduces possible contamination typically found in a vacuum system. In addition, particle contamination within the manifold, for example, from the sample itself, if it is a fine powder, is minimized, since the sample chamber pressure is not always under vacuum pressure conditions.

Sorption analysis is performed at one or more relative pressure points from 0 to 1. The sorption analysis can be performed at fixed pressure points equivalent to the required relative pressures, by the incremental increase of pressure from the pressure source. Although these fixed pressure points can be calculated from the predetermined relative pressure points, relative to the saturation pressure, this is not required by this invention. More specifically, one can choose relative pressures of 0.04, 0.08, 0.12, 0.16 and 0.20; however, the present invention permits a broader variation of relative pressures to be used. That is, if the majority of relative pressure points are between 0.05 and 0.35, one can employ additional relative pressure points which do not correspond to the addition of the adsorptive in successive equal increments. Typically, at least one data point should be determined and more preferably five data points, depending upon the degree of accuracy desired. If only a single data point is to be employed, it would be measured at approximately 0.3 relative pressure.

By way of example, and not limitation, typical relative pressure points which can be employed when using ten atmospheres of pressure, could correspond to five selected relative pressure values of 0.1, 0.15, 0.20, 0.25 and 0.30. These would correspond to absolute pressures of 1.0, 1.5, 2.0, 2.5 and 3.0 atmospheres, respectively.

As noted previously, the temperature of the adsorptive can change slightly due to environmental conditions of the liquid nitrogen bathe More specifically, the temperature of the liquid nitrogen, held in a dewar flask, always is found to be somewhat different than the normal boiling point, because of dissolved impurities from the atmosphere and because of ambient pressure fluctuations. Dissolved impurities usually increase the bath temperature sufficiently to cause the vapor pressure of pure liquid nitrogen within the sample cell to increase by 10 to 20 mm Hg above ambient pressure. The prior art has compensated for this by adding 15 mm Hg to ambient pressure, to give the correct saturated pressure to within 5 mm Hg. More specifically, when the prior art employs absolute pressures from 0 to 760 mm Hg in the analysis of the sample, a correction of 15 mm Hg might be meaningful for the precision required.

However, according to the present method, the saturation vapor pressure is measured and the correction factor is not used when using the elevated temperatures disclosed herein. For example, when using ten atmospheres of pressure as the saturation pressure, a correction of 15 mm Hg does not provide meaningful significance. In addition, the use of a pressurized container for the cooling medium virtually eliminates atmospheric contamination and the subsequent temperature change associated with an open dewar of the prior art.

A typical dosing scheme according to the present method would utilize a simple pressure regulator/control to sequentially increase and maintain the dose pressure constant at a value slightly higher than the sample pressure equilibrium point desired. A simple factory-calibrated manifold of small volume, for example 5 to 25 ml, would cumulatively add gas doses until the pressure above the sample approximates that in the dose volume. A summation of the total number of doses is a direct measure of the volume of gas adsorbed at the relative pressure for that data point.

The obtaining of the relative pressure is simplified if a large buffer volume of the adsorptive is employed. Typically, this buffer volume will be 2 to 100, preferably 5 to 50 times and most preferably 5 to 20 times the volume of the doser unit volume. The use of a large buffer volume enables the doser unit to be filled to a predetermined pressure, which permits successive doses with a minimal pressure drop, so that recharging of the buffer is minimized. More specifically, a large buffer volume can reduce the operating time of analysis. Controlling the pressure slightly greater than the value equivalent to the target relative pressure eliminates the constant adjustment of dose pressure and the subsequent stabilization time which is necessary with conventional subatmospheric pressures. The pressure is typically one to ten percent greater than the target relative pressure, so as to allow for the adsorption of the adsorptive gas. The dosing rate can be applied as rapidly as equilibration time will allow, which substantially reduces the analysis time for a multi-point BET surface area determination.

The sample measurement throughput is dependent upon many different factors. The total sample measurement period can be considered to comprise the following main sections: outgassing of the sample, setup of the sample measurement conditions, adsorptive dosing time, sample/adsorptive equilibration time, and sample results and post-processing time. An advantage of the present method is attributed to the use of higher absolute sample pressures. The increase in pressures from the prior art vacuum pressures to those of the present method, for example 0 to 15 atmospheres, provides a substantial decrease in the sample processing time, by decreasing the time taken to equilibrate the sample pressure during each adsorptive dose. An explanation for this decrease in equilibration time can be explained by considering the kinetic theory of gases for the formation of the monolayer portion of the isotherm. The premise derived by Langmuir in 1916 is that at adsorption equilibrium, a state of dynamic equilibrium exists when the number of gas molecules adsorbing (condensing) equals the number of gas molecules desorbing (evaporating).

In addition, the number of adsorptive molecules colliding with the surface of a solid adsorbent, $N_S$, which is freely exposed, increases with increasing pressure, P. This can be represented by the following theoretical calculations.

$$N_S = \frac{N_A P}{(2\pi MRT)^{\frac{1}{2}}}$$ Equation 1.

where
$N_A$ = Avogadro's number
$M$ = Adsorptive molecular weight
$T$ = Absolute temperature
$R$ = Universal gas constant When the temperature T is increased, the pressure of adsorptive needed to provide a given relative pressure, $P/P_o$, on the adsorption isotherm will increase proportionally with the adsorptive vapor pressure at temperature, T. To evaluate the relative collision rates of adsorptive molecules with adsorbent surfaces with increasing temperature, one might substitute the saturation vapor pressure, $P_o$, for the absolute pressure, P in Equation 1 above. Consideration of the number of adsorptive collisions with this substitution in Equation 1 at both 77K and 104K, yields an 8.6 fold increase at the higher temperature. Presumably, not only will the rate of surface collisions increase at higher temperatures and the adsorption rate, but also the rate of desorption or evaporation will also increase with increasing temperature.

The rate of desorption of molecules from the surface, $N_{DES}$ is given in Equation 2:

$$N_{DES} = Z_m \Theta_1 \nu_1 e^{-E/RT}$$ Equation 2 where
$Z_m$ = Number of adsorption sites per unit area
$\Theta$ = Fraction of sites occupied
$\nu_1$ = Frequency of oscillation of molecule in a normal to the surface
$E$ = Energy of adsorption If one assumes the energy of adsorption is constant for equivalent conditions at different temperatures of interest, then assessment of the relative rates of desorption can be made. However, one must first consider the change in the molecular vibrational frequency, $\nu_1$, with temperature. From the kinetic theory of gases:

$$\nu_1 = \frac{1}{2\pi}\sqrt{\frac{3RT}{M}}$$ Equation 3.

When the appropriate substitution of the frequency of vibration, calculated from Equation 3, is substituted into Equation 2, the relative change in desorption rate can be calculated. Increasing the temperature from 77K to 104K increases the desorption rate from the adsorptive surface by a factor of 1.6.

In summary, the rate of surface collisions and the rate of adsorption increases by a factor of 8.6 when going from a temperature of 77K to 100K. However, the rate of desorption also increases, but by only a factor of 1.6. The overall increase in rate of equilibration for a monolayer type coverage can be predicted to be (8.6/1.6) = 5.38.

The foregoing mathematical treatment is based upon the kinetic theory of gases and its applicability is limited to monolayer formation only. It is intended to illustrate, by way of example, a simple mechanism to illustrate the speed advantages obtained with this invention. A more detailed study is provided below by way of empirical timings related to various instruments.

The following Table 4 compares total processing time, including sample outgassing time, to three current instruments. The first one is marketed by Coulter Corporation, Hialeah, Fla. (Omnisorp 100); the second is by Micromeritics Instrument Corporation, Norcross, Ga. (Micromeritics ASAP 2400); and third is by Quantachrome Corporation, Syosset, N.Y. (Nova 1000); with the present invention, hereby designated as the SASCAds method (Super Atmospheric, Sub-Critical Adsorption) method.

TABLE 4

Comparison of Approximate Measurement Times in Minutes
Sample: NBS Alumina 0.15 g,
Adsorption and Desorption Isotherm Outgas Temperature: 300° C.
Analysis type: Static equilibrated.

| Analysis Mode | Coulter Omnisorp Model 100 | Micromeritics ASAP 2400 | Quantachrome Nova 1000 | SASCAds |
|---|---|---|---|---|
| #Adsorption Points | 36 | 44 | 25 | 95 |
| #Desorption Points | 25 | 46 | 14 | 55 |
| Outgas | 180 | 180 | 180 | 180 |
| Setup | 15 | 23 | 5 | 5 |
| Helium Calibration | 60 | 120 | 0 | 5 |
| Adsorptive Dose & Equilibration | 168 | 1745 | 185 | 210 |
| Finish Up | 5 | 5 | 5 | 5 |
| Reports | 15 | 5 | 5 | 5 |
| Total, excluding outgas | 263 | 1898 | 200 | 230 |
| Total, including outgas | 443 | 2078 | 380 | 410 |
| Time for each Data Point | 7.3 | 23.1 | 9.7 | 2.7 |

In the SASCAds method, the temperature of the adsorbate should be kept constant within 1K, preferably within 0.5K, more preferably within 0.2K and most preferably within 0.1K during the sorption isotherm measurement. One method for providing a stable cryostatic temperature employs an alternate adsorptive cryostatic bath. More specifically, a liquid oxygen bath, having a boiling point of 90K at one atmosphere, can be employed to raise the temperature of a nitrogen adsorptive which would have a boiling point below that temperature. Another example would be a liquid argon bath, having a boiling point of 87.5K at one atmosphere. Yet another example would be a liquid methane bath having a boiling point of 111.5K.

An alternate method to increase the temperature of the adsorptive gas greater than its normal boiling point at atmospheric pressure includes the use of liquid thermostat baths produced by using a stirred solid-liquid mixture at its melting point. However, these chemical baths typically are toxic and can present additional considerations to human safety and environmental hazards.

The following table gives the melting points of some readily available organic liquids suitable for cooling the adsorptive. The compounds are listed in order of their increasing melting points. Temperatures are in degrees Celsius.

TABLE 5

| Compound | Melting Point |
|---|---|
| Isopentane (2-methyl butane) | −159.9 |
| Methyl cyclopentane | −142.4 |
| Allyl chloride | −134.5 |
| n-Pentane | −129.7 |
| Allyl alcohol | −129 |

TABLE 5-continued

| Compound | Melting Point |
| --- | --- |
| Ethyl alcohol | −117.3 |
| Carbon disulfide | −110.8 |
| Isobutyl alcohol | −108 |
| Acetone | −95.4 |
| Toluene | −95 |

Another alternate method to increase the temperature of the adsorptive includes the use of commercially available equipment known to those skilled in the art to maintain the desired temperature. An example of such equipment is provided in U.S. Pat. No. 3,176,473. However, such equipment typically is quite expensive to obtain and operate.

A further method to increase the temperature of the adsorptive includes the use of a conventional dewar, which is fitted with a top and thus can be pressurized in order to raise the pressure in the dewar; and therefore allow for a rise in the dewar bath temperature when additional heat is provided.

The most desirable method to increase the temperature of the adsorptive greater than the boiling point at the environmental atmospheric pressure is to use the same compound for the adsorptive gas and the liquid cooling bath. The liquid cooling bath will be contained in a pressurizable chamber. As the pressure is increased in the cooling bath, the temperature likewise will increase, although additional heat might be required to obtain the required temperature at the selected pressure. More specifically, to increase the adsorptive temperature to the elevated value, the required increase in pressure can provide sufficient heat to raise the temperature of the bath to the required value at the selected pressure. Conversely, as the pressure is decreased, the temperature likewise will decrease.

By controlling the pressure of the cooling bath, one is effectively able to provide the conditions for controlling the temperature of the sample chamber. Although this is an acceptable method to accomplish the increase in temperature of the adsorptive, care must be exercised when increasing or decreasing the pressure to maintain a stable temperature.

A preferred apparatus to increase the temperature of the adsorptive greater than its boiling point at the environmental atmospheric pressure is depicted in FIG. 1. The apparatus comprises three chambers. The first chamber comprises two portions, a sample holder 2 and a conduit 4, through which the adsorptive is passed and introduced into the sample holder. The second chamber 6, an inner chamber, surrounds the first chamber and is connected to a conduit 7, through which adsorptive is passed and introduced into the inner chamber at a desired pressure. The third chamber 8, an outer chamber, surrounds the second chamber and is connected to a conduit 9, through which a variable heat transfer bridge is formed which separates the inner chamber from a conventional cryogenic liquid bath (not shown) in which it is positioned.

The sample holder 2 is inserted into the inner chamber 6 and is secured by a retaining ring 10. The inner chamber 6 can be integrally manufactured within the outer chamber 8.

The volume of the first chamber is accurately determined in accordance with conventional volumetric analytical procedures and the ideal gas law. The sample holder 2 can be sealed vacuum tight using a stopper valve 11 and is removable from the inner chamber 6, outer chamber 8, and the conduits 4, 7 and 9 of the apparatus. Thus, as a matter of convenience, weighing, outgassing and evacuation of the sample is conducted normally in the sample holder, while it is disconnected from the second and third chambers. Thereafter, the sealed, evacuated sample holder 2 is connected with the conduit 4 portion of the apparatus and is inserted into the second chamber 6, the inner chamber.

In accordance with conventional volumetric gas sorption analytical procedures, the volume of the sample holder is selected to be from about 1 to about 40, preferably 1 to 20, times the volume of the sample, to assure an accurate determination of the reference or blank for both adsorption and desorption, to minimize error which can be introduced into the line volume value at the liquid bath-air interface by fluctuations in the liquid nitrogen level, and to minimize error in determining the density of the sample. If the sample holder is too large, the accuracy of measurement will be adversely affected.

The temperature of the adsorptive in the sample holder is assumed to be the same as the temperature of the sample holder. In the preferred apparatus, this is achieved by having the sample holder 2 placed centrally into the closed, pressurizable, cryogenic, inner chamber 6. As discussed previously, by controlling the pressure in this inner chamber, the sample temperature can be controlled effectively. Most specifically and preferably, the inner chamber is filled with the same material used for the adsorptive. By continuously monitoring the temperature of the pressurizable cryogenic inner chamber, the pressure can be increased or decreased to adjust for fluctuations in the sample chamber temperature. The temperature can be measured by a temperature probe 12, which is located in the inner chamber 6. An electronically controlled pressure regulator 14 can be used to set the pressure and consequently the temperature of the sample. The pressure regulator 14 provides gas through the conduit 7, the outlet 16 of which is positioned near the bottom of the inner chamber 6. Gas passing through this tube is therefore bubbled through any liquid present. This stabilizing mechanism provides heat to the system in order to raise the liquid temperature, and also provides mixing of the liquid.

Surrounding this inner chamber is the outer chamber 8, which provides a variable heat transfer bridge from its external surface to a conventional cryogenic liquid bath (not shown) in which it is positioned. More specifically, the outer chamber can be a vacuum or can be filled with one or more substances which will provide a rapid heat transfer medium to transfer heat from the inner chamber to the cryogenic liquid bath. Such substances can include the same compound as used for the adsorptive, helium and any other gas which would not liquify the adsorptive or cause the adsorptive to condensate on the sample chamber walls.

A particular advantage of the preferred apparatus is that the outer chamber 8 can have a dual function. After it has transferred the heat from the inner chamber 6 to the cryogenic liquid bath, it is evacuated so as to act as an insulated dewar. This contributes to the ability to maintain the inner chamber and sample holder at a constant temperature.

When using liquid nitrogen in the outer chamber, and submersing it in a conventional liquid nitrogen cryogenic bath, the sample temperature can be controlled from approximately 77K to 130K. The preferred temperature range of the sample, when using nitrogen gas as the adsorptive and in the pressurizable inner chamber, and employing a liquid nitrogen cooling bath surrounding the outer chamber, is from 78K to 125K, preferably from 80K to 110K and most preferably from 90K to 105K.

It is to be understood that the present invention is not limited to any particular mathematical model for using the information embodied in either the adsorption or desorption isotherm, and such information can be manipulated as desired in accordance with any conventional procedure. However, the preferred method to determine the surface area pore volume and pore size distribution is according to the well known principles as described in U.S. Pat. No. 4,489,593 to Pieters, et al. More specifically, surface area analysis is conducted through determining a number of points which enable a least squares fit of the BET equation to be accomplished. As appreciated by those skilled in the art, when determining the surface area and other morphological surface characteristics of the solid material, consideration must be made for the increase in the kinetic diameter of the adsorbate at the increased temperature of the present method. More specifically, as the operating temperature is increased, the size of the adsorbate molecule must be determined for use with the BET equation. This adjustment can be mathematically or empirically derived. For the purposes of explanation, using nitrogen as the adsorbate, it is recognized that one nitrogen molecule at its boiling point of 77K occupies a surface area of 16.2 angstroms$^2$ on an adsorbent surface.

Since the present invention employs temperatures greater than 77K of the adsorptive, the surface area of the adsorbate molecule can be calibrated by the use of a solid having a known surface area. More specifically, an alumina support having a total surface area of 158 m/gram, as measured at 77K, is measured at the increased operating temperature of this invention; and the cross-sectional area of the adsorbate is determined from the number of adsorbate molecules required to produce a monolayer on the adsorbent.

The following example is the measurement sequence for the measurement of an adsorption isotherm for the purpose of surface area determination.

EXAMPLE 1

1. The sample is placed in the sample chamber 2 and its weight is recorded. The sample chamber is evacuated at an elevated temperature, typically 100° to 350° C. for three hours. This process of "outgassing" the sample removes pre-adsorbed gases and vapors. The sample chamber stopper valve 11 is then closed, thereby maintaining the vacuum present in the sample chamber.

2. The sample chamber then is inserted into the inner chamber 6 and the retaining ring 10 is tightened. The inner chamber 6 is integrally manufactured within the outer chamber 8.

3. The measurement procedure is commenced by lowering the assembled chambers 2, 6 and 8 into a bath of liquid nitrogen and then filling the outer chamber 8 with helium at a pressure of approximately 50 psia. The helium provides a rapid heat transfer medium for cooling the sample with the external liquid nitrogen bath.

4. Next, the inner chamber is pressurized with nitrogen gas to a positive pressure, which can typically be 100 psia. The temperature inside the inner chamber can be measured with the temperature probe 12. Liquefaction begins to take place inside the inner chamber.

When the temperature has dropped to the required value for analysis, in approximately two to three minutes, the outer chamber is evacuated and the sample temperature is stabilized by the liquid nitrogen formed within the inner chamber.

5. A helium dose is introduced into a manifold (not shown) to a pressure of approximately 20 psia and the equilibrium pressure is recorded. Then, this dose of helium is permitted to expand into the sample chamber 2, when the stopper valve 11 is opened. Equilibrium pressure is established and the new pressure is recorded. This dosing procedure is repeated two or more times and the "dead space" value determined. Helium is a non-adsorbing gas and is ideal for determination of the volume in the sample chamber. This helium calibration procedure requires approximately one to two minutes, due to the relatively high pressures used. Then the helium is evacuated. The adsorption measurement now commences.

6. Cumulative doses of the adsorptive nitrogen are adsorbed onto the sample and points of the isotherm are obtained by progressively increasing the equilibration pressure in the sample chamber. The volume of gas adsorbed is calculated by subtracting the dead space volume from the volume of nitrogen adsorptive dosed to the sample. This isotherm data is used then to calculate the specific surface area of the sample, using the BET equation.

EXAMPLE 2

Figure 2:
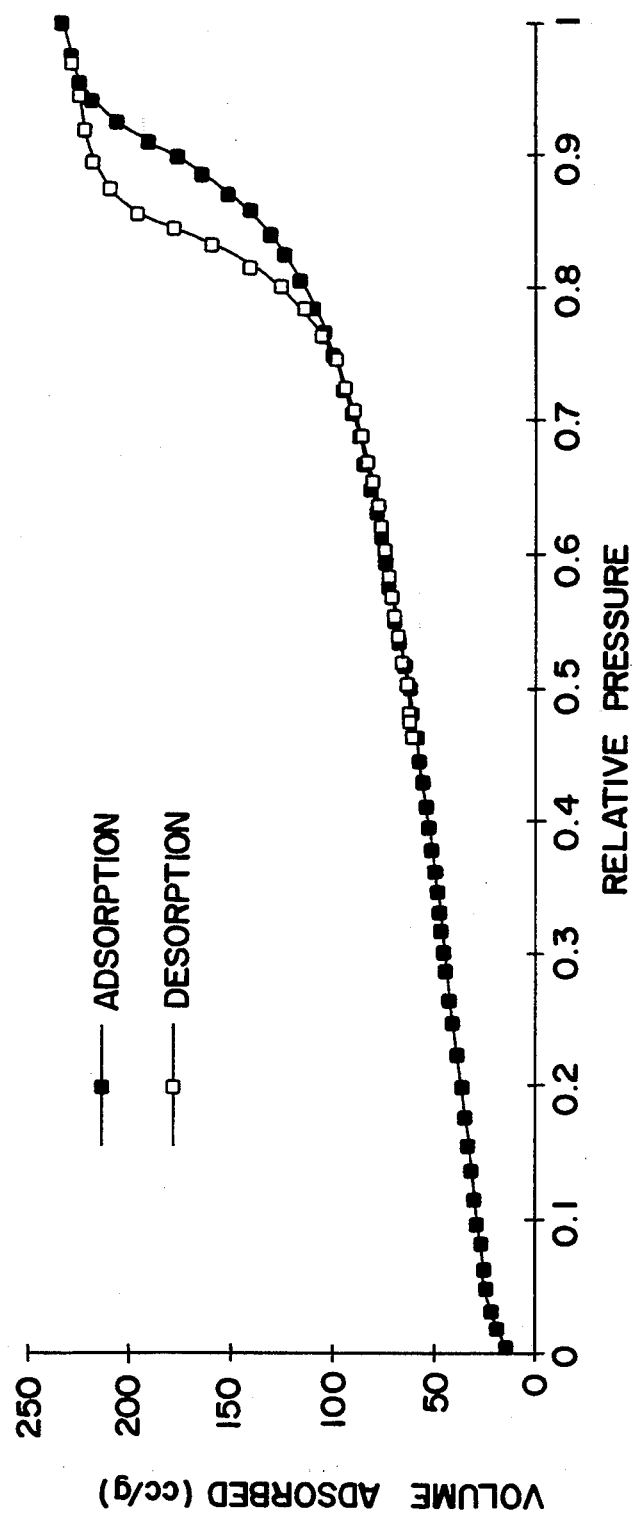
FIG. 2 is an example of an adsorption and desorption isotherm developed from a static (fully equilibrated) method.

Table 6 depicts actual data obtained when analyzing a National Bureau of Standards (NBS) alumina sample by the static equilibrated method. In this example, 58 data points were obtained for the adsorption isotherm, and 29 data points were obtained for the desorption isotherm. For convenience, only 14 data points are reported in Table 6. An isotherm using all data points can be constructed similarly to that shown in FIG. 2.

The following parameters were utilized in this example.

| | |
|---|---|
| Adsorbate | $N_2$ |
| Sample type | NBS alumina |
| Sample weight | .1205 grams |
| Liquid $N_2$ pressure | 70 psig |
| Sample chamber set temperature | 96K |
| Equilibration time interval | 5 seconds |

TABLE 6

| Point | Dose (mm Hg) | Pressure (mm Hg) | Temperature (K) | Po (mm Hg) | P/Po | Vol Ads (cc/g) |
|---|---|---|---|---|---|---|
| 1 | 162.19 | 21.21 | 95.894 | 4381.9 | .005 | 14.183 |
| 2 | 741.71 | 599.80 | 95.900 | 4383.9 | .137 | 31.804 |
| 3 | 1496.7 | 1389.7 | 95.862 | 4371.1 | .318 | 46.392 |
| 4 | 2149.8 | 2027.0 | 95.889 | 4380.2 | .463 | 58.782 |
| 5 | 2881.3 | 2743.1 | 95.877 | 4376.1 | .627 | 78.094 |
| 6 | 3693.6 | 3516.5 | 95.861 | 4370.7 | .805 | 115.86 |
| 7 | 4321.8 | 4105.9 | 95.829 | 4359.8 | .942 | 219.15 |
| 8 | 4540.1 | 4364.3 | 95.851 | 4367.3 | .999 | 234.25 |
| 9 | 3929.8 | 4129.7 | 95.859 | 4370.0 | .945 | 225.45 |
| 10 | 3526.4 | 3747.7 | 95.882 | 4377.9 | .856 | 195.96 |
| 11 | 2940.8 | 3093.8 | 95.872 | 4374.6 | .707 | 89.433 |
| 12 | 2588.2 | 2708.4 | 95.837 | 4362.7 | .621 | 76.048 |
| 13 | 2330.7 | 2435.9 | 95.898 | 4383.4 | .556 | 69.357 |
| 14 | 1940.0 | 2040.1 | 95.631 | 4293.4 | .475 | 61.915 |

Wherein:
Po = saturation pressure
P/Po = relative pressure

Vol Ads = volume of adsorptive in cubic centimeters per gram

In addition, the sorption isotherm can be constructed using the continuous flow techniques taught by U.S. Pat. No. 4,489,593 to Pieters, et al. As taught by Pieters, et al., an evacuated chamber of known volume and maintained at a known substantially constant temperature containing the outgassed sample is provided. To this chamber is introduced, preferably continuously, the adsorptive gas at a known substantially constant mass flow rate, preferably for a time sufficient to achieve an adsorptive gas relative pressure of at least 0.20, and most preferably for a time sufficient to condense at least a portion of the adsorptive gas on the adsorbent (i.e. at a relative pressure from 0 to 1) while establishing the pressure of the adsorptive gas within the chamber as a function of time as it is so introduced. This pressure is referred to herein as the sampled chamber pressure.

The mass flow rate at which the adsorptive gas is introduced into the chamber is selected to be not greater than the equilibration rate of adsorption of the adsorptive gas by the adsorbent. More specifically, for any given set of conditions of volume, temperature, pressure, and amount of adsorptive gas in contact with the adsorbent, the rate at which the molecules of the adsorptive gas strike and are adsorbed by the adsorbent will eventually equal the rate at which the adsorbed adsorptive gas molecules leave the surface of the adsorbent. When this occurs, the rate of adsorption is referred to herein as the equilibration rate of adsorption.

At conditions of constant volume and temperature, the establishment of this equilibrium is observed by constant pressure (i.e. a fluctuation of not greater than ±0.25 percent of the pressure) of the adsorptive gas over a period of time, e.g. about 20 to 40 minutes. If the mass flow rate employed is greater than the equilibration rate of adsorption and administration of the adsorptive gas is interrupted, it will take a finite period of time until the pressure in the chamber becomes constant. However, if the mass flow rate is not greater than the equilibration rate of adsorption and adsorptive gas administration is interrupted, the pressure will be constant from the time of interruption. By controlling the mass flow rate to be not greater than the equilibration rate of adsorption, the pressure established at any given time during the introduction of the adsorptive gas, will be the equilibrium pressure.

Consequently, by establishing the equilibrium pressure of the adsorptive gas as it is introduced into the sample chamber as a function of time, the equilibrium pressure is equated with the sampled chamber pressure. As such, one skilled in the art is able to correlate: (a) the sampled chamber pressure; (b) the adsorptive gas mass flow rate; and (c) the time needed to attain said sampled chamber pressure with the amount of adsorptive gas adsorbed by the adsorbent at said sampled chamber pressure to develop the sorption isotherm. The resulting adsorption isotherm is a plot of the amount of adsorptive gas adsorbed by the adsorbent at a given equilibrium pressure.

EXAMPLE 3

In this illustrative embodiment of continuous flow adsorption, like the previous disclosed Example 2 static equilibrated adsorption embodiment, the adsorptive is at a temperature which is greater than its boiling point at the environmental atmospheric pressure. The adsorptive gas has a saturation vapor pressure greater than the its saturation vapor pressure at the environmental atmospheric pressure. To facilitate this increase in temperature and pressure, the same preferred apparatus described in Example 1 can be employed. A summary of the appropriate parameters employed is provided in Table 7.

TABLE 7

| | |
|---|---|
| Adsorptive | $N_2$ |
| Sample type | NBS alumina |
| Sample weight | 0.083 grams |
| Saturation Pressure | 5,300 mm Hg |
| Conduit line volume | 10.7 cc |
| Sample chamber volume | calculated from He calibration |
| Liquid $N_2$ bath temperature | 77.2K |
| Sample chamber temperature | 98.6K |
| Mass flow rate | 0.30 ml/min |
| Relative pressure range | 0 to 0.3 |
| Total number of pressure/time data points sampled | 1000 |
| Determined surface area | 159 $m_2/g$ |

The desorption mode is the reverse of the adsorption mode. The desorption mode employs a solid sample, referred to as the desorbent, the morphological characteristics of which are sought to be determined, and a gas or liquid referred to herein as the desorbate. The desorbate is desorbed from the sample during the desorption mode, the desorbate being thereafter referred to as the desorptive. Therefore, the desorption mode employs a starting sample material, which has been first outgassed as described herein, and then its surface and any pores present are contacted with an adsorptive in a manner sufficient to condense the adsorptive on the sample material, fill the pores, and coat the outer surface of the sample material with at least a monolayer of condensed desorbate. As a matter of convenience, the sample material typically is saturated with an adsorbate to ensure complete filling of the sample pores. Upon the completion of condensing the gas on the sample material, it is referred to as the desorbate. Thus, the terms "desorptive" and "desorbate" are used in place of "adsorptive" and "adsorbate" merely to identify the mode in which the gas or liquid constituting that substance is employed. The materials which can constitute the adsorptive and the desorptive are the same. Like the adsorptive, the desorptive gas can comprise a single component gas and an inert carrier gas. Preferably, the desorptive gas comprises at least 80 percent of a single component gas and less than 20 percent of a carrier gas. Most preferably, the desorptive gas comprises a single gas without a carrier gas.

Accordingly, to conduct the desorption mode, a chamber of known volume and temperature, as described in accordance with the adsorption mode, is provided with a sample having desorbate condensed thereon and in equilibrium with a chamber atmosphere consisting of gaseous desorptive. This typically is performed by conducting the adsorption mode until sample saturation is achieved as described hereinabove.

EXAMPLE 4

In this illustrative embodiment of desorption by continuous flow, the desorptive is at a temperature which is greater than the corresponding boiling point of the desorptive gas at environmental atmospheric pressure. The desorptive gas has a saturation vapor pressure greater than the corresponding saturation vapor pressure of said desorptive gas at environmental atmospheric pressure. To facilitate this increase in temperature and pressure, the same preferred apparatus described in Example 1 can be employed. A summary of the appropriate parameters employed is provided in Table 8.

TABLE 8

| | |
|---|---|
| Desorbate | N$_2$ |
| Sample type | NBS Alumina |
| Sample weight | 0.080 grams |
| Saturation pressure | 4340 mm Hg |
| Conduit line volume | 10.7 cc |
| Sample chamber volume | Calculated from He calibration |
| Liquid N$_2$ bath temperature | 77.2K |
| Sample chamber temperature | 96.0K |
| Mass flow rate | 0.30 ml/min |
| Relative pressure range | 0.994 to 0.487 |
| Total number of pressure/time data points sampled | 14,300 |
| Mean pore size | 43 angstroms radius |

The principles, preferred embodiments, and modes of operation of the present invention have been described in the foregoing specification. The invention which is intended to be protected herein, however, is not to be construed as limited to the particular forms disclosed, since these are to be regarded as illustrative rather than restrictive. Variations and changes can be made by those skilled in the art without departing from the spirit of the invention.

What is claimed is:

1. A method of analyzing the characteristics of an adsorbent which comprises:
   a. providing a sample chamber of known volume and known temperature with an adsorbent to be analyzed;
   b. introducing into said sample chamber an adsorptive gas which comprises at least 80 percent of a component gas and less than 20 percent of a carrier gas, at a temperature higher than its boiling point at environmental atmospheric pressure;
   c. measuring the pressure of said adsorptive gas;
   d. determining the quantity of said adsorptive gas adsorbed by said adsorbent, at said measured pressure; and
   e. correlating a relative pressure in said sample chamber and said quantity of the adsorptive gas adsorbed by said adsorbent at said relative pressure.

2. The method of claim 1 wherein said adsorptive gas has a saturation vapor pressure higher than its saturation vapor pressure at environmental atmospheric pressure.

3. The method of claim 2 wherein said adsorptive gas has a saturation vapor pressure greater than 0.05 atmospheres above its saturation vapor pressure at atmospheric pressure.

4. The method of claim 1 wherein said adsorptive gas has a temperature higher than 0.2K above its boiling point at atmospheric pressure.

5. The method of claim 4 wherein said temperature of said adsorptive gas changes less than 0.5K.

6. The method of claim 5 wherein said sample chamber is surrounded by at least one other chamber which contains a pressurized gas.

7. The method of claim 6 wherein said adsorptive gas has a temperature from 78K to 125K.

8. The method of claim 4 wherein said adsorptive gas is nitrogen.

9. A method of analyzing the characteristics of an adsorbent which comprises:
   a. providing a sample chamber of known volume and known temperature with an adsorbent to be analyzed;
   b. introducing into said sample chamber an adsorptive gas which comprises at least 80 percent of a component gas and less than 20 percent of a carrier gas, at a temperature higher than its boiling point at environmental atmospheric pressure, and at a known mass flow rate for a time sufficient to obtain adsorption of at least a portion of said adsorptive gas by said adsorbent, said known mass flow rate being not greater than the equilibration rate of adsorption of said adsorptive gas by said adsorbent;
   c. establishing the equilibrium pressure of said adsorptive gas as it is introduced into said sample chamber as a function of time, said equilibrium pressure being a sampled chamber pressure; and
   d. correlating the sampled chamber pressure, the adsorptive gas mass flow rate, and the time needed to attain said sampled chamber pressure with the amount of adsorptive gas adsorbed by the adsorbent at said sampled chamber pressure.

10. The method of claim 9 wherein said adsorptive gas has a saturation vapor pressure higher than its saturation vapor pressure at environmental atmospheric pressure.

11. The method of claim 10 wherein said adsorptive gas has a saturation vapor pressure greater than 0.05 atmospheres above its saturation vapor pressure at atmospheric pressure.

12. The method of claim 9 wherein said adsorptive gas has a temperature greater than 0.2K its boiling point at atmospheric pressure.

13. The method of claim 12 wherein said adsorptive gas is nitrogen.

14. A method of analyzing the characteristics of a desorbent which comprises:
   a. providing a sample chamber of known volume and known temperature with a desorbent for analysis, said desorbent having a desorptive gas condensed thereon;
   b. withdrawing from said sample chamber said desorptive gas, said desorptive gas comprising at least 80 percent of a single component gas and less than 20 percent of a carrier gas, at a temperature higher than its boiling point at environmental atmospheric pressure;
   c. measuring the pressure of said desorptive gas;
   d. determining the quantity of said desorptive gas desorbed by said desorbent, at said measured pressure; and
   e. correlating a relative pressure in said sample chamber and said quantity of the desorptive gas desorbed by said desorbent at said relative pressure.

15. The method of claim 14 wherein said desorptive gas has a saturation vapor pressure higher than its saturation vapor pressure at atmospheric pressure.

16. The method of claim 15 wherein said desorptive gas has a saturation vapor pressure higher than 0.5 atmospheres above its saturation vapor pressure at atmospheric pressure.

17. The method of claim 14 wherein said desorptive gas has a temperature higher than 0.2K above its boiling point at atmospheric pressure.

18. The method of claim 17 wherein said desorptive gas is nitrogen.

19. The method of analyzing the characteristics of a desorbent which comprises:

a. providing a sample chamber of known volume and known temperature with a desorbent for analysis, said desorbent having a desorptive gas condensed thereon and in equilibrium with a chamber atmosphere consisting of said desorptive gas;

b. withdrawing from said sample chamber said desorptive gas, said desorptive gas comprising at least 80 percent of a component gas and less than 20 percent of a carrier gas, at a temperature higher than its boiling point at environmental atmospheric pressure, at a known mass flow rate which is not greater than the equilibration rate of desorption of the desorptive gas from the desorbent for a time sufficient to obtain desorption of at least a portion of said desorptive gas by the desorbent;

c. establishing the equilibrium pressure of said desorptive gas as it is withdrawn from said sample chamber as a function of time, said equilibrium pressure being a desorptive gas sampled chamber pressure; and d. correlating the sampled pressure, the desorptive gas mass flow rate, and the time needed to attain said sampled chamber pressure with the amount of desorptive gas desorbed by the desorbent at said sampled chamber pressure.

20. The method of claim 19 wherein said desorptive gas has a saturation vapor pressure higher than its saturation vapor pressure at environmental atmospheric pressure.

21. The method of claim 20 wherein said desorptive gas has a saturation vapor pressure greater than 0.05 atmospheres above its saturation vapor pressure at atmospheric pressure.

22. The method of claim 19 wherein said desorptive gas has a temperature greater than 0.2K above its boiling point at atmospheric pressure.

23. The method of claim 22 wherein said desorptive gas is nitrogen.

* * * * *